US00PP12447P2

(12) United States Plant Patent
Turc

(10) Patent No.: US PP12,447 P2
(45) Date of Patent: Mar. 12, 2002

(54) ALSTROEMERIA PLANT NAMED 'LOIRIANJ'

(75) Inventor: Jean Pierre Turc, Mazé (FR)

(73) Assignee: Selection New Plant Sarl, Le Luc (FR)

( * ) Notice: Subject to any disclaimer, the term of this patent is extended or adjusted under 35 U.S.C. 154(b) by 0 days.

(21) Appl. No.: 09/610,609

(22) Filed: Jul. 5, 2000

(51) Int. Cl.[7] ..... A01H 5/00
(52) U.S. Cl. ..... Plt./309
(58) Field of Search ..... Plt./309

(56) References Cited

U.S. PATENT DOCUMENTS

PP3,281 P * 1/1973 van Staaveren ..... Plt./309
PP4,599 P * 10/1980 van Staaveren ..... Plt./309
PP8,668 P * 3/1994 van Andel ..... Plt./309
PP8,739 P * 5/1994 van Andel ..... Plt./309

OTHER PUBLICATIONS

UPOV–ROM GTITM Computer Database, 2000/06, GTI Jouve Retrieval Software, citation for 'Loirianj'.*
Protection Des Obtentions Vegetales, Bulletin Officiel du Comité de la Protection des Obtentions Végétales, pp. 497, 498, 503 and 504 (Nov. 10, 1996).
LOIRINCA, Les Alstroemeres Turcieflor published by Les Richelets, 49630 Maze, France prior to Jul. 5, 1999 (four pages).

* cited by examiner

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct variety of Alstroemeria plant of tall height is provided which forms on a substantially continuous basis attractive large yellow-orange flowers (as illustrated). The flowers are borne on upright peduncles and display brownish streaks on the petals. The plant propagates well by the division of roots. The new variety can be grown as a distinctive ornamental plant.

1 Drawing Sheet

SUMMARY OF THE INVENTION

The new variety of Alstroemeria plant was created by artificial pollination wherein two parents were crossed which previously had been studied in the hope that they would contribute the desired characteristics. The female parent (i.e., the seed parent) of the new variety was '92102' variety (non-patented in the United States). The male parent (i.e., the pollen parent) of the new variety was the '9039D' variety (non-patented in the United States). The parentage of the new variety can be summarized as follows:

'92102'×'9039D'.

The seeds resulting from the above pollination were sown and small plants were obtained which were physically and biologically different from each other. Selective study resulted in the identification of a single plant of the new variety.

It was found that the new Alstroemeria plant of the present invention possesses the following combination of characteristics:

(a) Forms on a substantially continuous basis attractive large yellow-orange flowers having brownish streaks on the petals that are borne on upright peduncles,
(b) Exhibits a tall plant height,
(c) Propagates well by the division of roots, and
(d) Is particularly suited for growing as a distinctive ornamental plant.

The new variety of the present invention readily can be distinguished from its parental varieties. For instance '92102' parent forms light pink blossoms, forms stocky stems and short peduncles, and assumes a height of only approximately one meter. The '9030D' parent forms dissimilar bright orange blossoms and assumes a height of only approximately 1.5 meter.

The new variety well meets the needs of the horticultural industry. It is particularly well-suited for use as attractive ornamentation in the landscape or for growing as a decorative pot plant.

The new variety has been found to undergo asexual propagation in France by the separation or splitting of roots. Asexual propagation by the above-mentioned methods as performed in France has shown that the characteristics of the new variety are strictly transmissible from one generation to another.

The new variety has been named the 'Loirianj' variety.

BRIEF DESCRIPTION OF THE PHOTOGRAPH

The accompanying photograph shows as nearly true as it is reasonably possible to make the same, in a color illustration of this character, a typical specimen of the new variety. The new variety of Alstroemeria plant was observed while growing in a greenhouse at Mazé, Maine et Loire, France. Fully opened blossoms, partially opened blossoms, foliage, peduncles, and stems are illustrated. The distinctive orange-yellow blossoms having brownish streaks on the petals are well displayed.

DETAILED DESCRIPTION

The chart used in the identification of the colors is that of The Royal Horticultural Society (R.H.S. Colour Chart). Color terminology is used in some instances to indicate the corresponding colors in more common terms that are to be accorded their ordinary dictionary significance. The description is based on the observation of eighteen month-old specimens of the new variety during May while growing in greenhouses at Mazé, Maine et Loire, France.

Origin: Artificial pollination.

Parentage:

*Female.*—'92102'.

*Male.*—'9039D'.

Classification: Alstroemeria Hybrid.

Plant:

*Form.*—Shrub.

*Height.*—Size: tall, approximately 1.6 to 2 m on average.

*Width.*—Approximately 1 m on average.

*Habit.*—Fast growing with vigorous upright stems of good strength.

*Stems.*—Approximately 60 to 75 stems are formed per year. An eighteen month-old plant commonly will have approximately 90 to 110 stems on average.

Foliage:

*Leaf shape.*—Lanceolate.

*Leaf size.*—Approximately 18 cm in length and approximately 3.5 cm in width.

*Leaf apex.*—Acuminate.

*Leaf base.*—Attenuate.

*Texture.*—Glossy on upper surface.

*Margin.*—Entire.

*Quantity.*—Approximately 15 to 20 leaves per stem on average.

*Color.*—Adult foliage is medium green, Green Group 137A on the upper surface, and near Greyed-Green Group 189A on the under surface.

*Vein pattern.*—Substantially parallel.

*Vein color.*—Green Group 139A.

*Rhizome color.*—White, near White Group 155D.

*Rhizome size.*—Variable with the growing season.

*Petiole length.*—Commonly less than one centimeter.

*Petiole diameter.*—Approximately one centimeter on average.

*Petiole color.*—Green group 137A.

Inflorescence:

*Peduncle length.*—Commonly approximately 12 to 13 cm.

*Petiole diameter.*—Approximately 3 to 5 mm on average.

*Peduncle disposition.*—Erect and stiff.

*Petiole texture.*—Smooth.

*Peduncle color.*—Yellow-green group 144A, and suffused at times with claret, greyed-purple group 184B, coloration.

*Buds.*—Shape: oblong and pear-shaped. Color: Green Group 137A. Size: approximately 4.5 cm in length, and approximately 1.5 cm in diameter.

*Blooming habit.*—Continuous with no substantial interruption.

*Blooms.*—Size: large. Diameter: approximately 6.5 cm. Depth: approximately 4 cm. Borne: commonly singly on a stem. Form: cup-shaped. Number of petals: three internal petals and three external tepals that have the appearance of petals. Arrangement: generally two concentric circles of three petals and three tepals. Texture: soft. Appearance: satiny. Configuration: Central petals: elongated with a pointed, sometimes cuspidate, tip and a narrow base, the margin is slightly serrated, the length is approximately 5 to 6 cm, and the width is approximately 1 to 1.5 cm. External tepals: substantially round and emarginate with a narrowing base, the margin is slightly serrated, the length is approximately 5 to 6 cm, and the width is approximately 3 to 4 cm. Color (in course of opening): Central petals (obverse): at the tip Yellow-Orange Group 14A with brownish streaks of near Greyed-Orange Group 176C, and at the base grooved and near Greyed-Purple Group 184A in coloration. Central petals (reverse): at the tip Yellow Group 13A and more brown, Greyed-Purple Group 184B, towards the base. External tepals (obverse): Yellow Group 13B towards the tip, some Red Group 39B towards the central portion, and then some Yellow Group 13B. External tepals (reverse): Yellow Group 13B towards the tip, and some Red Group 42B towards the central portion with some greenish, Green Group 137B, small veins. Color (after full bloom): lightening, Yellow Group 11C, tends to occur. Blooming period: throughout the year at Loire, France. Lasting quality: approximately 4 to 5 weeks on the plant, and approximately 3 weeks when the blossoms are cut and are placed in a vase. Stamens: commonly six in number with one being arranged opposite each petal. Anthers: before dehiscence greenish-brown, Yellow-Green Group 152B, in coloration and after dehiscence changing to brown coloration, Grey-Brown Group 199A, and commonly approximately 8 mm. in length. Filaments: Orange-Red Group 31B in coloration and approximately 4 cm in length. Pollen: yellow-orange, Greyed-Orange Group 164B in coloration. Pistils: commonly one. Styles: Orange-Red Group 34D in coloration and approximately 2.5 cm in length. Stigmas: orange, Yellow-Orange Group 22B, in coloration. Fragrance: none observed. Fruit: greenish-brown in coloration at maturity, rounded, and commonly infertile.

Development:

*Propagation.*—Propagates well through the division of roots.

*Resistance to diseases.*—Good with respect to traditional diseases under greenhouse growing conditions.

*Resistance to insects.*—Typical of species.

*Resistance to heat and dought.*—Typical of species.

*Resistance to frost.*—None and typical of species.

I claim:

1. A new and distinct variety of Alstroemeria plant characterized by the following combination of characteristics:

(a) Forms on a substantially continuous basis attractive large yellow-orange flowers having brownish streaks on the petals that are borne on upright peduncles, (b) Exhibits a tall plant height;

(c) Propagates well by the division of roots; and (d) Is particularly suited for growing as a distinctive ornamental plant;

substantially as herein shown and described.

* * * * *

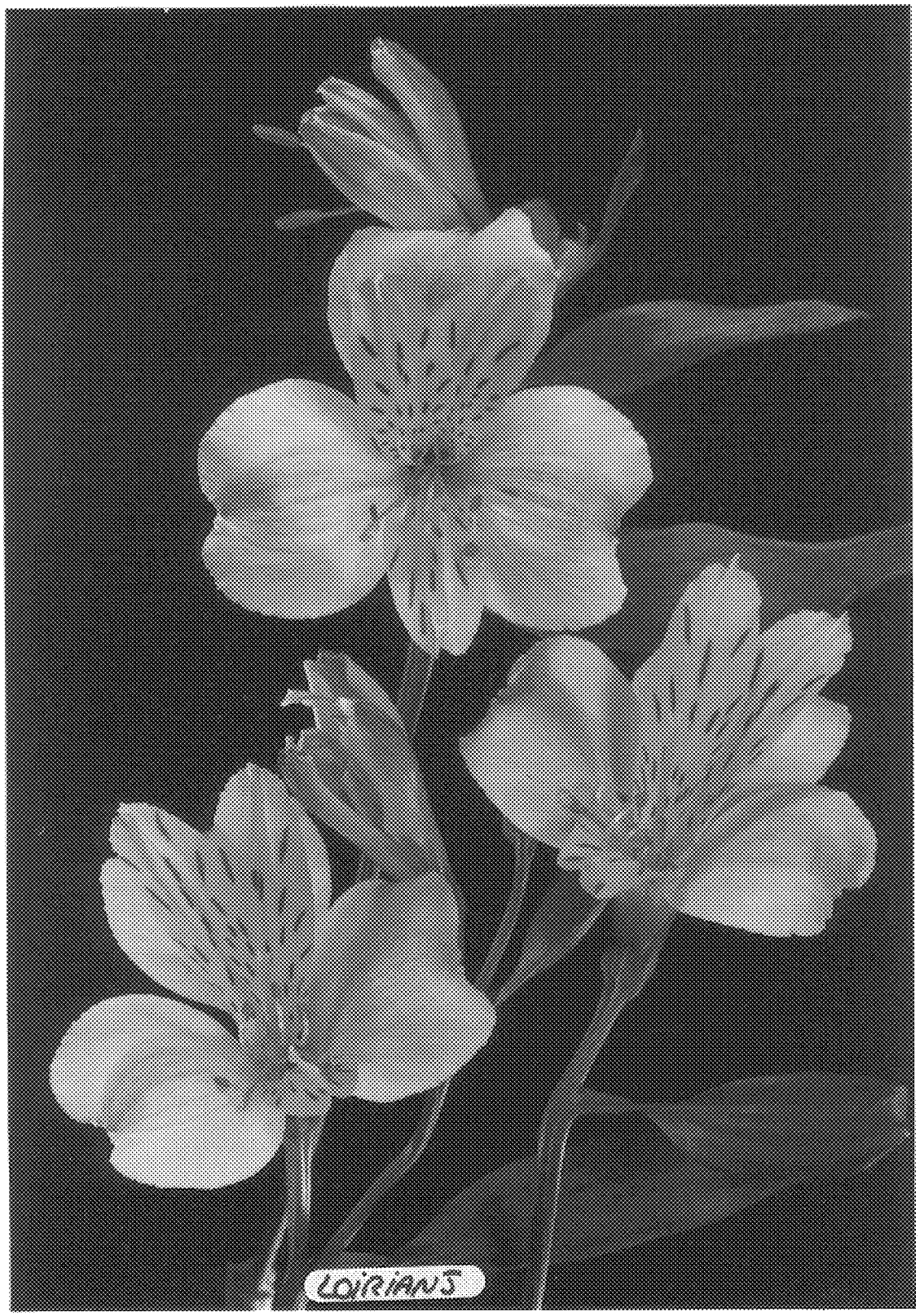
LOIRIANS